(12) United States Patent
Uchikawa et al.

(10) Patent No.: US 7,302,828 B2
(45) Date of Patent: Dec. 4, 2007

(54) OXYGEN SENSOR (75) Inventors: Akira Uchikawa, Gunma (JP); Masao Tsukada, Gunma (JP); Shoichi Sakai, Gunma (JP); Masami Kawashima, Gunma (JP); Keiji Mori, Gunma (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/227,063

(22) Filed: Sep. 16, 2005

(65) Prior Publication Data

US 2006/0086175 A1    Apr. 27, 2006

(30) Foreign Application Priority Data

Oct. 27, 2004   (JP)   ............... 2004-312081

(51) Int. Cl.
    *G01N 7/00*    (2006.01)
(52) U.S. Cl. ...................... 73/23.31; 73/23.2
(58) Field of Classification Search ............... 73/200, 73/23.31, 23.2; 219/543, 548, 552
    See application file for complete search history.

(56) References Cited

U.S. PATENT DOCUMENTS

| 6,194,693 | B1 * | 2/2001 | Shirai et al. ............... 219/552 |
| 6,258,234 | B1 | 7/2001 | Watanabe et al. |
| 6,340,809 | B2 * | 1/2002 | Yamada ..................... 219/543 |
| 6,866,517 | B2 * | 3/2005 | Kimata et al. ................ 439/33 |

FOREIGN PATENT DOCUMENTS

| JP | 09-178694 A | 7/1997 |
| JP | 9-178694 A | 7/1997 |
| JP | 2000-131270 A | 5/2000 |
| JP | 2000-199752 A | 7/2000 |
| JP | 2002 071627 A | 3/2002 |
| JP | 2002-131270 A | 5/2002 |
| JP | 2004-219268 A | 8/2004 |
| WO | WO 01/35087 A2 | 5/2001 |

* cited by examiner

*Primary Examiner*—Hezron Williams
*Assistant Examiner*—Tamiko Bellamy
(74) *Attorney, Agent, or Firm*—Sughrue Mion, PLLC

(57) ABSTRACT

An oxygen sensor includes a tubular casing; an oxygen detecting element installed in a leading end of the tubular casing; lead wires each extending from the oxygen detecting element to the outside of the tubular casing through an open base end of the tubular casing, each lead wire including a core wire of metal; a rubber bush plugged in the open base end of the tubular casing, the rubber bush having the lead wires passed therethrough; and a heat resisting structure for protecting the rubber bush from a high temperature. The heat resisting structure is constructed to satisfy the following inequality:

$$10\% \leq Al/Ar \leq 50\%,$$

wherein:
    Al: The sectional area in total of the lead wires; and
    Ar: The sectional area of the rubber bush.

12 Claims, 5 Drawing Sheets

OXYGEN SENSOR

BACKGROUND OF THE INVENTION

1. Field of the Invention

The present invention relates in general to oxygen sensors, and more particularly to the oxygen sensors of a type that is suitable for sensing an oxygen concentration in an exhaust gas discharged from automotive internal combustion engines.

2. Description of the Related Art

Hitherto, various types of oxygen sensors have been proposed and put into practical use particularly in the field of automotive internal combustion engines.

One of such oxygen sensors is shown in Japanese Laid-open Patent Application (Tokkaihei) 9-178694. The oxygen sensor of the publication generally comprises a tubular casing that has an open base end, an oxygen detector unit that is installed in the tubular casing, a rubber bush that is plugged in the open base end of the tubular casing, and lead wires that extend from the oxygen detector unit to the outside of the tubular casing through the rubber bush.

In use, for measuring the amount of oxygen in the exhaust gas, the oxygen sensor is installed in the exhaust manifold or exhaust pipe which is highly heated under operation of the engine. That is, under operation of the engine, the rubber bush is kept subjected to a heat attack. Thus, usually, the rubber bush is made of a heat resistant type, the rubber bush is positioned away from the highly heated head portion of the tubular casing by increasing the length of the casing and/or the rubber bush is protected from the high heat by using a separate heat protecting member.

SUMMARY OF THE INVENTION

However, even the above-mentioned measures for avoiding the severe heat attack to the rubber bush have failed to exhibit a satisfied result particularly in case wherein the exhaust gas from the engine is greatly high in temperature and/or elongation of the tubular casing is not practically possible due to a limited space where the oxygen sensor is positioned. Actually, in case of the motorcycles, it is quite difficult to provide the exhaust system of the engine with a space sufficient for locating such oxygen sensor. Of course, hitherto, various measures have been proposed and put into practical use for protecting the rubber bush from such high heat. However, because of difficulty in putting the measures into practical use, almost all of them have caused increase in production cost of the oxygen sensor.

Accordingly, an object of the present invention is to provide an oxygen sensor that is free of the above-mentioned drawbacks.

That is, a main object of the present invention is to provide an oxygen sensor that is constructed to protect the rubber bush from high heat by practically using the lead wires as a heat transmitting and radiation means.

In accordance with a first aspect of the present invention, there is provided an oxygen sensor which comprises a tubular casing; an oxygen detecting element installed in a leading end of the tubular casing; lead wires each extending from the oxygen detecting element to the outside of the tubular casing through an open base end of the tubular casing, each lead wire including a core wire of metal; a rubber bush plugged in the open base end of the tubular casing, the rubber bush having the lead wires passed therethrough; and a heat resisting structure for protecting the rubber bush from a high temperature, wherein the heat resisting structure is constructed to satisfy the following inequality:

$$10\% \leq Al/Ar \leq 50\%$$

wherein:

Al: The sectional area in total of the lead wires.

Ar: The sectional area of the rubber bush.

In accordance with a second aspect of the present invention, there is provided an oxygen sensor which comprises a tubular casing; an oxygen detecting element installed in a heading end of the tubular casing; lead wires each extending from the oxygen detecting element to the outside of the tubular casing though an open base end of the tubular casing, each lead wire including a core wire of metal; a rubber bush plugged in the open base end of the tubular casing, the rubber bush having the lead wires passed therethrough; and a heat resisting structure for protecting the rubber bush from a high temperature, wherein the heat resisting structure is constructed to satisfy the following inequality:

$$Ac/Al \geq 40\%$$

Wherein:

Ac: The sectional area in total of the core wires of the lead wires.

Al: The sectional area in total of the lead wires.

In accordance with a third aspect of the present invention, there is provided an oxygen sensor which comprises a tubular casing; an oxygen detecting element installed in a leading end of the tubular casing; lead wires each extending from the oxygen detecting element to the outside of the tubular casing through an open base end of the tubular casing, each lead wire including a core wire of metal; a rubber bush plugged in the open base end of the tubular casing, the rubber bush having the lead wires passed therethrough; and a heat resisting structure for protecting the rubber bush from a high temperature, wherein the heat resisting structure comprises a plurality of zones of the rubber bush that are equally partitioned, the number of zones corresponding to the number of the lead wires, each zone of the rubber bush having a center position through which the corresponding lead wire passes, and wherein the heat resisting structure is constructed to satisfy the following inequality:

$$10\% \leq Al/Ar \leq 50\%$$

wherein:

Al: The sectional area in total of the lead wires.

Ar: The sectional area of the rubber bush.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

In the following, the present invention will be described in detail with reference to the accompanying drawings.

For ease of understanding, various directional terms, such as right, left, upper, lower, rightward and the like are used in the following description. However, such terms are to be understood with respect to only the drawing or drawings on which a corresponding part or portion is shown.

Figure 1:
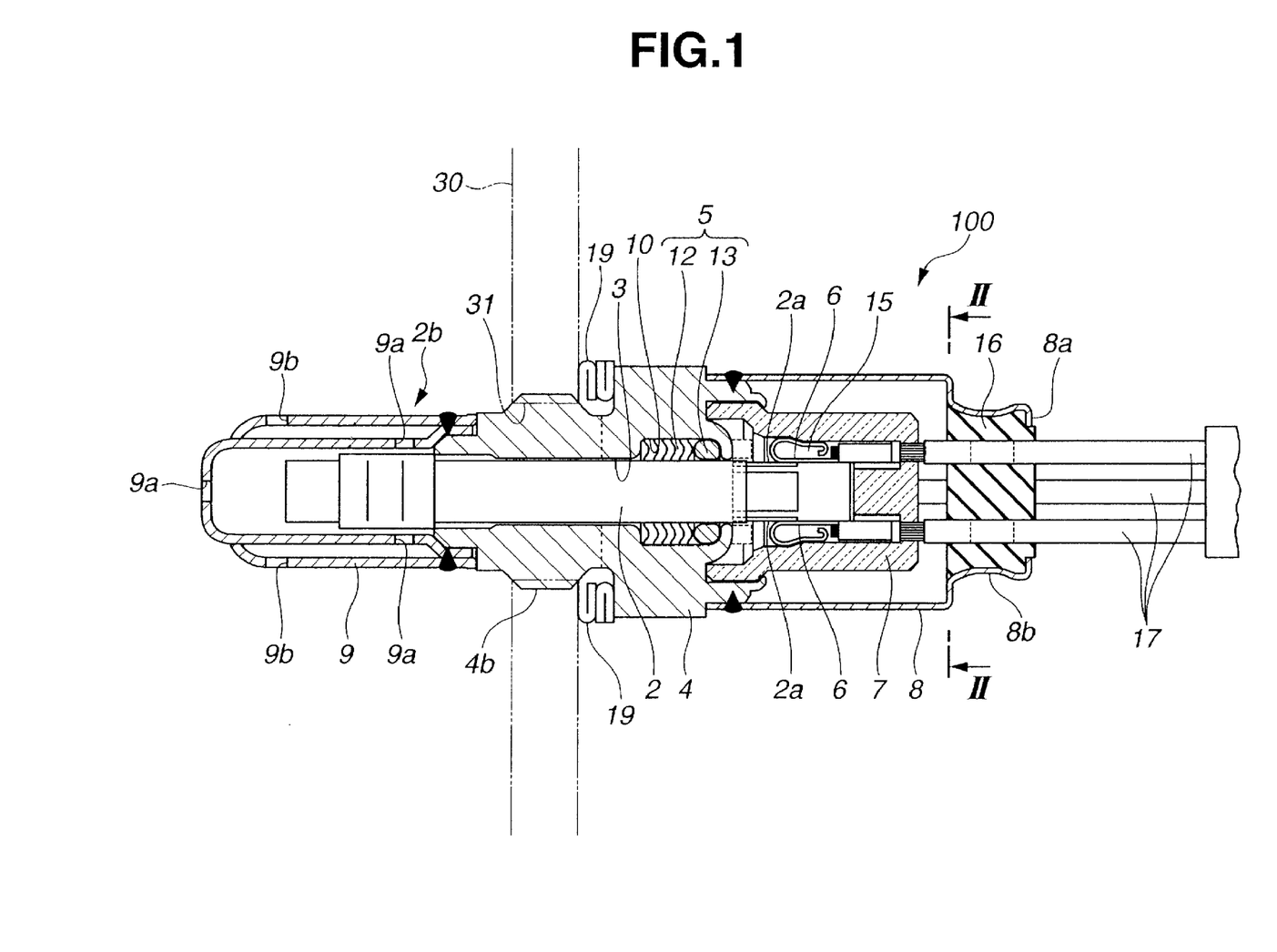
FIG. 1 is a sectional view of an oxygen sensor according to the present invention.
Figure 2:
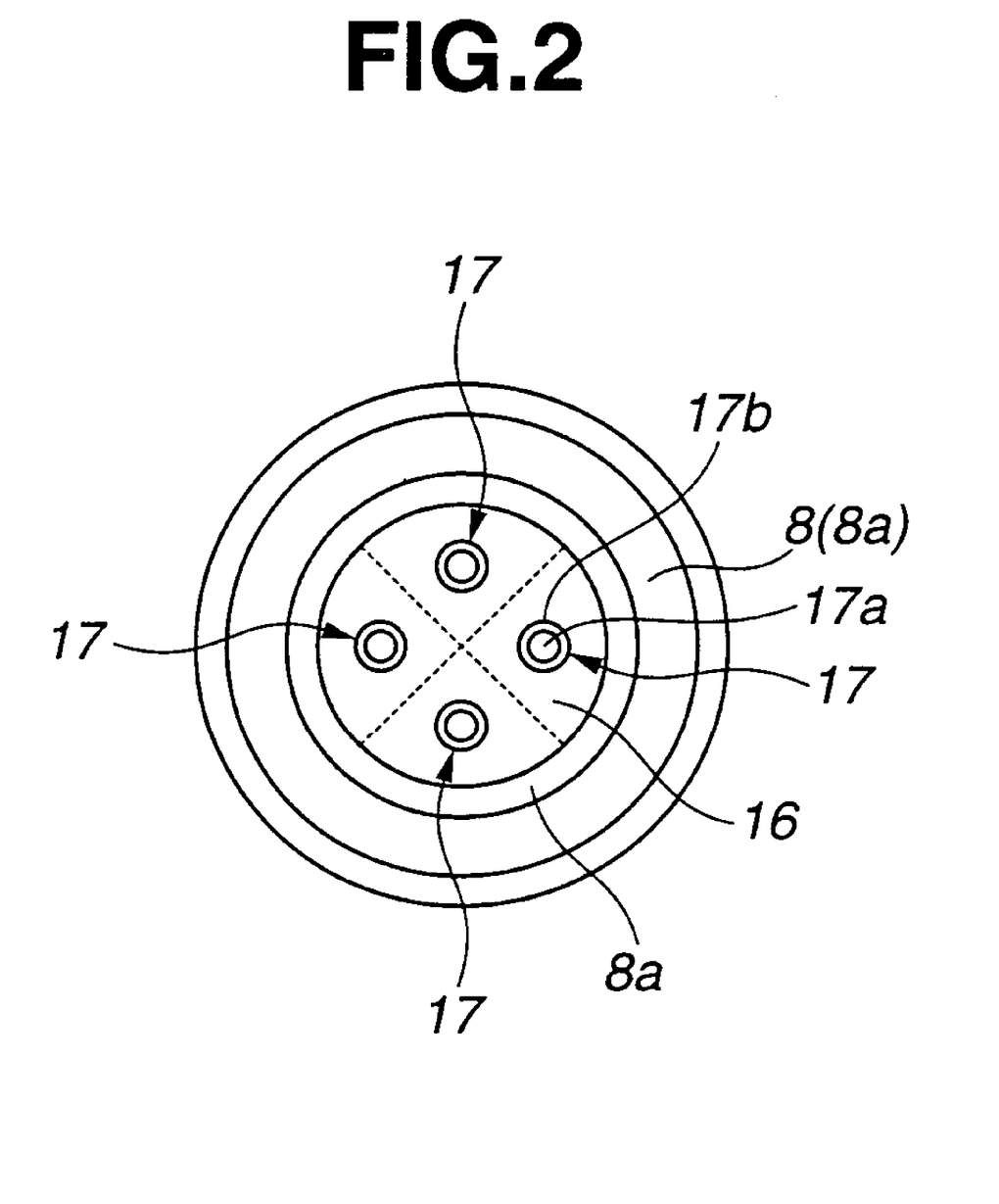
FIG. 2 is a sectional view taken along the line II-II of FIG. 1.

Referring to FIGS. 1 and 2, particularly FIG. 1, there is shown an oxygen sensor 100 according to the present invention.

In the disclosed example, the oxygen sensor 100 is used for sensing the oxygen concentration in the exhaust gas from an lo automotive internal combustion engine (not shown) and thus the sensor 100 is mounted to an exhaust pipe 30 that extends from the internal combustion engine.

As is seen from FIG. 1, the oxygen sensor 100 comprises a cylindrical holder 4 that has a cylindrical bore 3 formed therethrough, and a cylindrical rod member 2 that is intimately received in the cylindrical bore 3. As shown, the cylindrical rod member 2 has left and right end portions that are exposed to the outside of the cylindrical bore 3. The left end portion is provided with an oxygen detecting element 2b and the right end portion is provided with electrodes 2a. Although not well shown, between the oxygen detecting element 2b and each of the electrodes 2a, there extends a lead for electric connection therebetween.

The oxygen detecting element 2b is received in a double tube type protector 9 that has an open base end secured via welding, caulking or the like to the cylindrical holder 4.

As shown, the double tube type protector 9 comprises inner and outer tubes that are coupled together to form a cylindrical space therebetween. The inner and outer tubes are formed with small openings 9a and 9b through which part of the exhaust gas in the exhaust pipe 30 is led to the oxygen detecting element 2b.

The cylindrical bore 3 of the holder 4 is formed at a position near the electrodes 2a with a diametrically enlarged space portion 10 in which a sealing structure 5 is tightly installed for achieving a hermetical sealing between the cylindrical rod member 2 and the cylindrical bore 3.

The sealing structure 5 comprises a mass of ceramic powder 12 (for example, non-sintered talc or the like) contained in the enlarged space portion 10 and a washer 13 arranged to tightly pack the ceramic powder 12 in the enlarged space portion 10.

As shown, the right end of the cylindrical rod member 2 is tightly received in a cylindrical glass holder 7 that surrounds the electrodes 2a. A left end of the cylindrical glass holder 7 is tightly grasped by a holder portion defined by a right end of the cylindrical holder 4, as shown.

A cylindrical casing 8 that puts therein the cylindrical glass holder 7 has a left end secured, by means of laser beam welding, to the right peripheral end of the cylindrical holder 4. As shown, there is defined a cylindrical space between the glass holder 7 and the cylindrical casing 8. Due to the laser beam welding, the connected portion between the cylindrical casing 8 and the cylindrical holder 4 is hermetically sealed.

The cylindrical casing 8 has at its right side a diametrically reduced holder part 8b that has a cylindrical rubber bush 16 installed therein. The rubber bush 16 is constructed of a heat resistant material, such as fluoro rubber or the like. The holder part 8b of the cylindrical casing 8 has a flange 8a by which a right peripheral edge of the rubber bush 16 is tightly held.

As is best seen from FIG. 2, through the rubber bush 16, there extend four lead wires 17. Each lead wire 17 comprises a core wire 17a that is made of a metal and an insulator coating 17b that coats the core wire 17a.

Referring back to FIG. 1, because of the elasticity possessed by the rubber bush 16, a hermetical sealing is achieved between each lead wire 17 and the rubber bush 16 as well as between the rubber bush 16 and the cylindrical casing 8. That is, the cylindrical internal space defined between the glass holder 7 and the cylindrical casing 8 is hermetically isolated from the outside of the oxygen sensor 100.

As shown in FIG. 1, the lead wires 17 have at their left ends respective terminal members 6 that are held in the glass holder 7. Each terminal member 6 is constructed to show a resiliency by which the terminal member 6 is pressed against the corresponding electrode 2a to achieve a desired electric connection therebetween.

In use, the oxygen sensor 100 is mounted to the exhaust pipe 30 having the detecting side thereof (viz., the side of the double tube type protector 9) exposed to the interior of the exhaust pipe 30. For this mounting, the exhaust pipe 30 is formed with a threaded bore 31 with which a threaded portion 4b of the cylindrical holder 4 is tightly engaged. A gasket 19 is operatively disposed between the exhaust pipe 30 and the oxygen sensor 100 to obtain a hermetical sealing therebetween.

When, in operation, part of the exhaust gas flowing in the exhaust pipe 30 is led into the interior of the double tube type protector 9 through the small openings 9a and 9b, the oxygen detecting element 2b detects the amount of oxygen in the exhaust gas and issues a corresponding information signal. The information signal is led to an external electric device (not shown) through the leads, the electrodes 2a, the terminal members 6 and the lead wires 17.

In the following, important points and features of the present invention will be described in detail with reference to the drawings, especially FIGS. 3 to 5.

In the present invention, for the reasons that will become apparent as the description proceeds, each of the lead wires 17 (more specifically, the core wires 17a of the lead wires 17) is made thicker than a conventional lead wire such as one as disclosed in the above-mentioned publication (viz., Tokkaihei 9-178694). That is, by using such thicker lead wires 17, effective heat transmission and radiation of the lead wires 17 are obtained, which induces suppression of the rubber bush 16 from being excessively heated. That is, by using such thicker lead wires 17, improvement in the heat resistance of the rubber bush 16 is obtained, and thus undesired crack of the bush 16 is suppressed.

Figure 3:
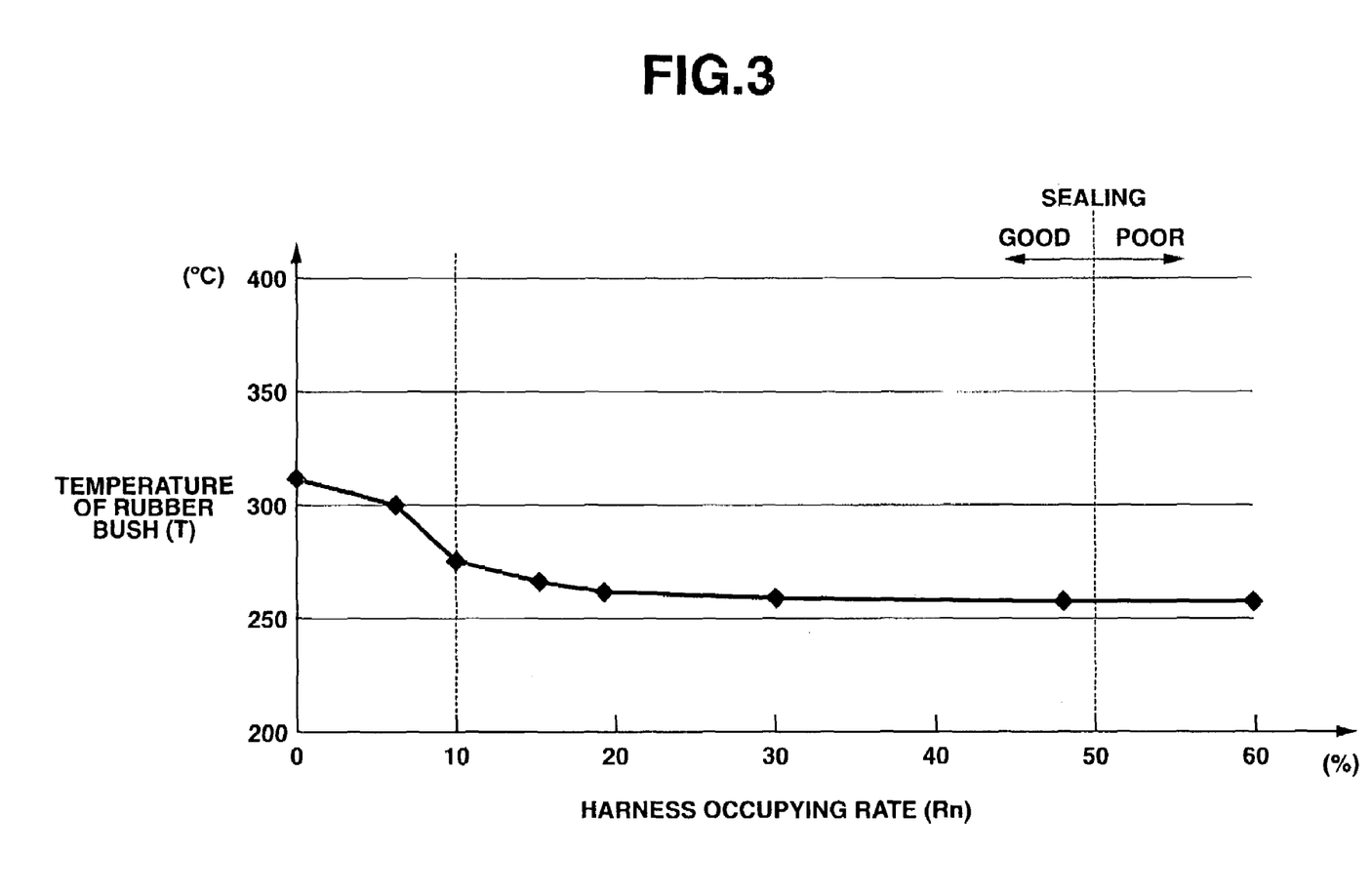
FIG. 3 is a graph showing a temperature lowering ability for a rubber bush of the oxygen sensor of the present invention in terms of a relationship between a harness occupying rate and a temperature of the rubber bush.

FIG. 3 is a graph depicting results of experiments carried out by the inventors for studying and providing a first embodiment of the present invention. For the experiments, various types of test pieces were prepared by the inventors, which were the same in construction as the oxygen sensor of FIG. 1 except the number and thickness of the lead wires 17.

In the graph of FIG. 3, the x-axis (viz., abscissa) represents a harness occupying rate "Rh" and the y-axis (viz., ordinate) represents a temperature "T" of the rubber bush 16.

The harness occupying rate "Rh" is calculated from the following equality:

$$Rh = Al/Ar \qquad (1)$$

wherein:

Al: The sectional area in total of the lead wires 17.

Ar: The sectional area of the rubber bush 16.

It is to be noted that the sectional area of each lead wire 17 and that of the rubber bush 16 were measured with respect to the area of the cross section that is defined to be perpendicular to the corresponding axis.

It is further to be noted that the temperature "T" of the rubber bush 16 was the temperature indicated by the rubber bush 16 of each test piece set to an exhaust pipe of which temperature was kept constant during the experiments.

It is further to be noted that each lead wire 17 used in the experiments was a coated wire that comprises a copper core wire 17a of which heat conductivity is 398 W/m·K and a coating 17b of fluororesin that coats the copper core wire 17a.

As is seen from the graph of FIG. 3, with increase of the harness occupying rate "Rh", that is, with increase in thickness of each lead wire 17, the temperature "T" of the rubber bush 16 was lowered. This means that with increase of the harness occupying rate "Rh", a so-called temperature lowering ability of the lead wires 17 for the rubber bush 16 is increased.

When the harness occupying rate "Rh" exceeded about 10%, the temperature lowering ability for the rubber bush 16 became constant while keeping a sufficient effect. Thus, in view of the temperature lowering effect, it is preferable to use the harness occupying rate "Rh" in a range that is higher than 10%.

However, when the harness occupying rate "Rh" exceeded about 50%, the sealing ability of the rubber bush 16 became poor. This may be caused by the lowering in elasticity of the rubber bush 16 due to reduction in volume of the same.

Additional experiments showed that when the harness occupying rate "Rh" was lower than 30%, that is, when 10%≦Al/Ar≦30% was established, the rubber bush 16 exhibited an excellent sealing ability.

From the above-described experiments, it has been revealed that when the harness occupying rate "Rh" is in the range from about 10% to about 50%, that is, when 10%≦Rh≦50% is established, the temperature lowering ability for the rubber bush 16 and the sealing ability of the rubber bush 16 are both ensured. Furthermore, it has been revealed that when the harness occupying rate "Rh" is in the range from about 10% to about 30%, that is, when 10%≦Rh≦30% is established, the rubber bush 16 exhibits an excellent sealing ability in addition to the sufficient temperature lowering ability.

The additional experiments further revealed that the temperature lowering ability for the rubber bush 16 and the sealing ability of the rubber bush 16 show their best values when the lead wires 17 are arranged in the rubber bush 16 at equally spaced intervals. Thus, as is seen from FIG. 2, if the lead wires 17 are four in number, the four lead wires 17 should be respectively positioned in four equal zones of the rubber bush 16, that are provided by dividing the sectional area of the rubber bush 16 by 90 degrees.

Figure 4:
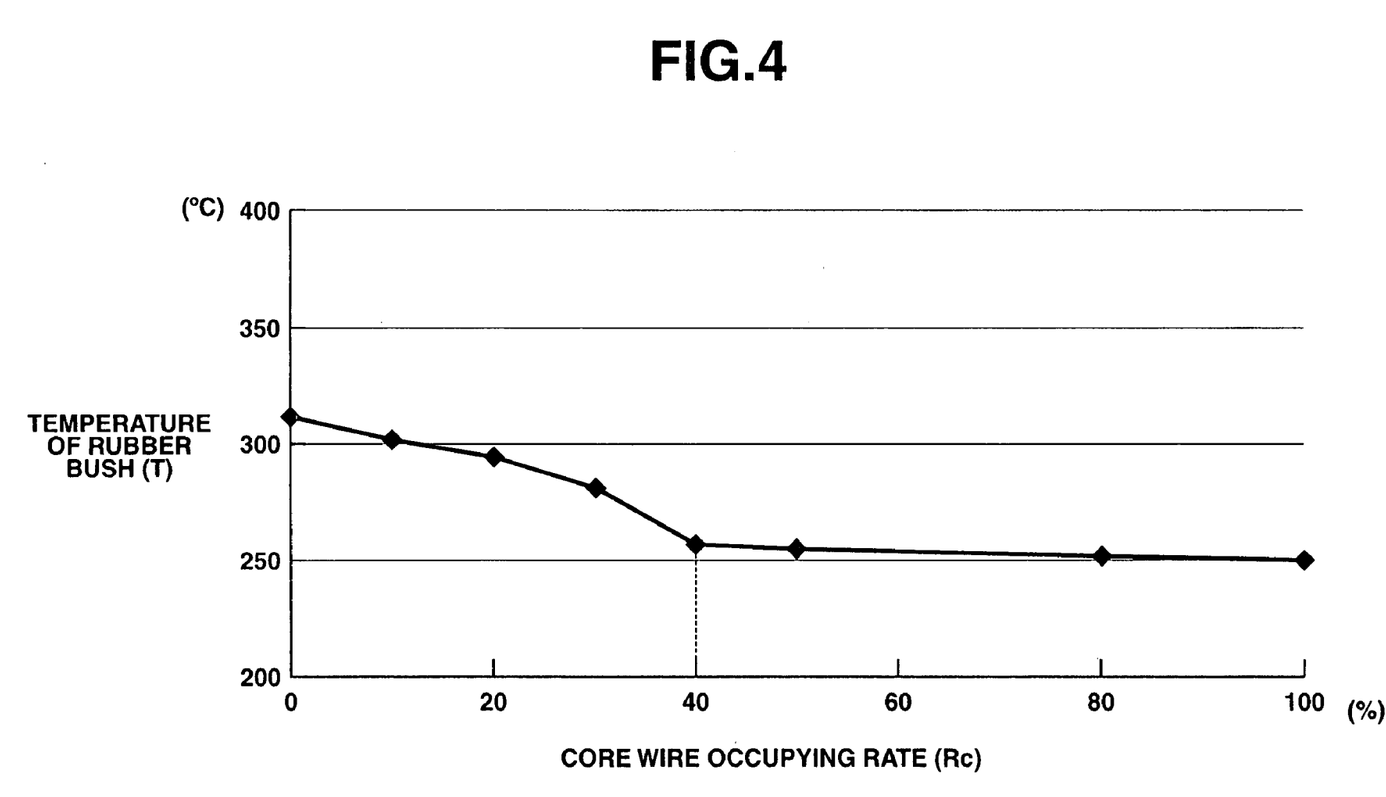
FIG. 4 is a graph showing the temperature lowering ability for the rubber bush of the oxygen sensor of the present invention in terms of a relationship between a core wire occupying rate and the temperature of the rubber bush.

FIG. 4 is a graph depicting results of other experiments carried out by the inventors for studying and providing a second embodiment of the present invention.

In the graph of FIG. 4, the x-axis (viz., abscissa) represents a core wire occupying rate "Rc" and the y-axis (viz., ordinate) represents a temperature "T" of the rubber bush 16.

The core wire occupying rate "Rc" is calculated from the following equation:

$$Ac/Al \qquad (2)$$

wherein:

Ac: The sectional area in total of the core wires 17a of the lead wires 17.

Al: The sectional area in total of t e lead wires 17.

As is seen from the graph of FIG. 4, with increase of the core wire occupying rate "Rc", that is, with increase in thickness of the core wire 17a of each lead wire 17, the temperature "T" of the rubber bush 16 was lowered. This means that with increase of the core wire occupying rate "Rc", the temperature lowering ability for the rubber bush 16 is increased.

When the core wire occupying rate "Rc" exceeded about 40%, the temperature lowering ability for the rubber bush 16 became constant while keeping a sufficient effect. Thus, in view of the temperature lowering effect, it is preferable to use the core wire occupying rate "Rc" in a range that is higher than 40%.

As is easily understood, when the core wire 17a becomes thinner, the heat transmission and radiation ability of the entire construction of the lead wire 17 is reduced, which makes the temperature lowering ability for the rubber bush 16 poorer. Of course, excessive thinning of the core wire 17a is not preferable in view of the electrical resistance too.

Figure 5:
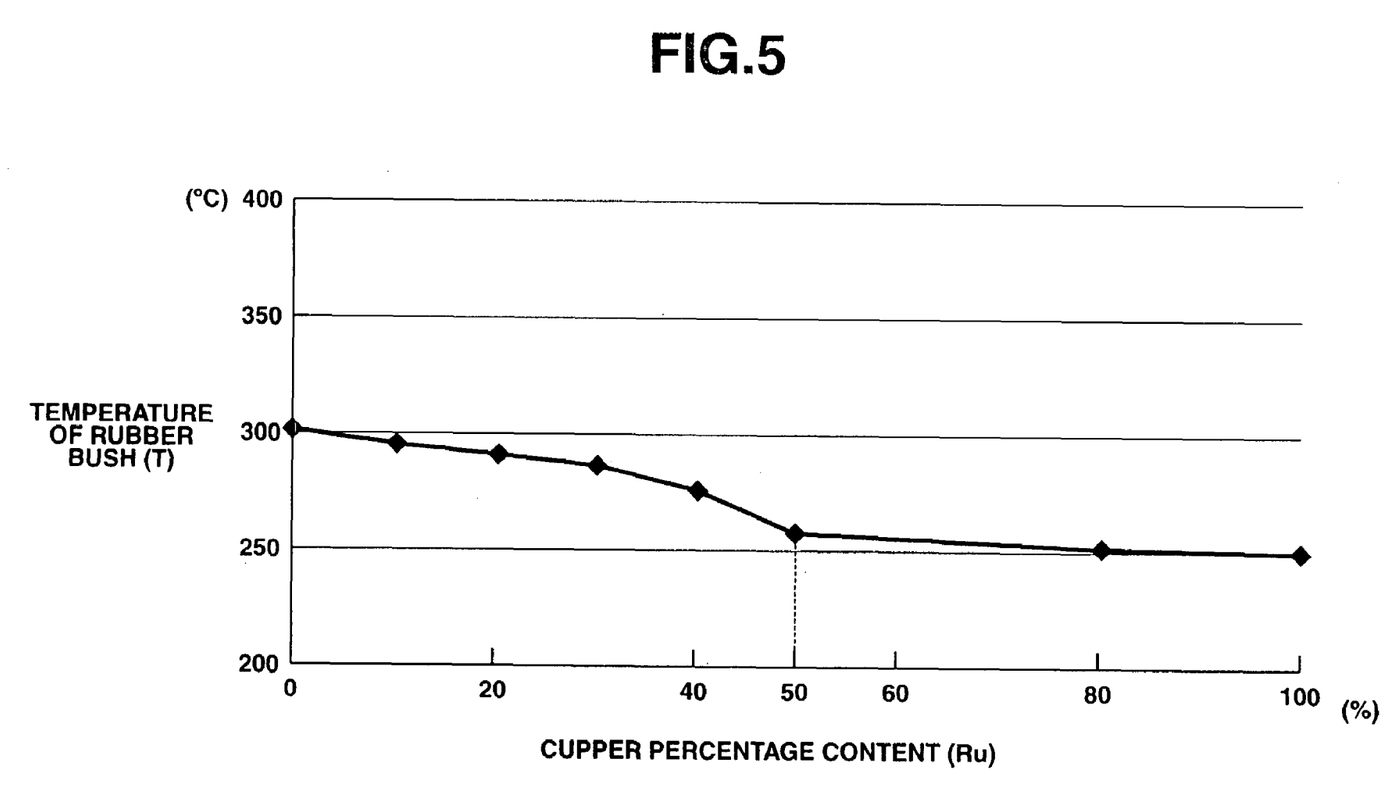
FIG. 5 is a graph showing the temperature lowering ability for the rubber bush of the oxygen sensor of the present invention in terms of a relationship between a cupper content by percentage of the core wire and the temperature of the rubber bush.

FIG. 5 is a graph depicting results of still other experiments carried out by the inventors for studying and providing a third embodiment of the present invention.

In the graph of FIG. 5, the x-axis (viz., abscissa) represents a cupper percentage content "Ru" and the y-axis (viz., ordinate) represents a temperature "T" of the rubber bush 16.

It is to be noted that the copper percentage content "Ru" is the weight percentage of copper contained in the core wire 17a of the lead wire 17. It is further to be noted that the core wire 17a used in the experiments was a combined wire member that comprises a copper wire of which heat conductivity is about 398 W/m·K and a stainless steel wire of which heat conductivity is about 23-W/m·K.

As is seen from the graph of FIG. 5, with increase of the copper percentage content "Ru", that is, with increase of the heat conductivity of the core wire 17a, the temperature "T" of the rubber bush 16 was lowered. This means that with increase of the copper percentage content "Ru", the temperature lowering ability for the rubber bush 16 is increased.

When the copper percentage content "Ru" exceeded about 50%, the temperature lowering ability for the rubber bush 16 became constant while keeping a sufficient effect. Thus, in view of the temperature lowering effect, it is preferable to use the copper percentage content "Ru" in a range that is higher than 50%.

As is easily understood, when the content of a higher conductivity metal is small in the core wire 17a, the heat transmission and radiation ability of the core wire 17a and that of the entire construction of the lead wire 17 are reduced, which makes the temperature lowering ability for the rubber bush 16 poorer. Metals that have a heat conductivity higher than 300 W/m·K are copper (Cu), silver (Ag) and gold (Au). Thus, as a material for economically producing the core wire 17a, brass, phosphor bronze and/or stainless steel plated with copper may be used.

As has been described hereinabove, when the harness occupying rate "Rh" is in the range from about 10% to about 50% (viz., first embodiment), the temperature lowering ability for the rubber bush 16 and the sealing ability of the rubber bush 16 are both ensured.

Furthermore, when the harness occupying rate "Rh" is in the range from about 10% to about 30%, the sealing ability of the rubber bush 16 becomes excellent in addition to sufficient temperature lowering ability for the rubber bush 16.

When the core wire occupying rate "Rc" takes a value exceeding 40% (viz., second embodiment), the temperature lowering ability for the rubber bush 16 is assured.

When the percentage content "Ru" of a metal of which heat conductivity is higher than 300 W/m·K takes a value exceeding 50% (viz., third embodiment), the temperature lowering ability for the rubber bush 16 is assured.

The entire contents of Japanese Patent Application 2004-312081 filed Oct. 27, 2004 are incorporated herein by reference.

Although the invention has been described above with reference to the embodiments of the invention, the invention is not limited to such embodiments as described above. Various modifications and variations of such embodiments may be carried out by those skilled in the art, in light of the above description.

What is claimed is:

1. An oxygen sensor comprising:
a tubular casing;
an oxygen detecting element installed in a leading end of the tubular casing;
lead wires each extending from the oxygen detecting element to the outside of the tubular casing through an open base end of the tubular casing, each lead wire including a core wire of metal;
a rubber bush plugged in the open base end of the tubular casing, the rubber bush having the lead wires passed therethrough; and
a heat resisting structure for protecting the rubber bush from a high temperature,
wherein the heat resisting structure is constructed to satisfy the following inequality:

$10\% \leq Al/Ar \leq 50\%$ wherein:
Al: The sectional area in total of the lead wires; and
Ar: The sectional area of the rubber bush.

2. An oxygen sensor as claimed in claim 1, in which the heat resisting structure is constructed to satisfy the following inequality:

$10\% \leq Al/Ar \leq 30\%$.

3. An oxygen sensor as claimed in claim 1, in which the heat resisting structure is constructed to satisfy the following inequality:

$Ac/Al \geq 40\%$ wherein:
Ac: The sectional area in total of the core wires of the lead wires; and
Al: The sectional area in total of the lead wires.

4. An oxygen sensor as claimed in claim 3, in which over 50% in weight percentage of the material of the core wires is constructed of a metal of which heat conductivity is higher than 300 W/m·K.

5. An oxygen sensor comprising:
a tubular casing;
an oxygen detecting element installed in a heading end of the tubular casing;
lead wires each extending from the oxygen detecting element to the outside of the tubular casing though an open base end of the tubular casing, each lead wire including a core wire of metal;
a rubber bush plugged in the open base end of the tubular casing, the rubber bush having the lead wires passed therethrough; and
a heat resisting structure for protecting the rubber bush from a high temperature,
wherein the heat resisting structure is constructed to satisfy the following inequality:

$Ac/Al \geq 40\%$ wherein:
Ac: The sectional area in total of the core wires of the lead wires; and
Al: The sectional area in total of the lead wires.

6. An oxygen sensor as claimed in claim 5, in which over 50% in weight percentage of the material of the core wires is constructed of a metal of which heat conductivity is higher than 300 W/m·K.

7. An oxygen sensor as claimed in claim 5, in which the material of the core wire of each lead wire is at least one of brass, phosphor bronze and stainless steel plated with copper.

8. An oxygen sensor comprising:
a tubular casing;
an oxygen detecting element installed in a leading end of the tubular casing;
lead wires each extending from the oxygen detecting element to the outside of the tubular casing through an open base end of the tubular casing, each lead wire including a core wire of metal;
a rubber bush plugged in the open base end of the tubular casing, the rubber bush having the lead wires passed therethrough; and
a heat resisting structure for protecting the rubber bush from a high temperature,
wherein the heat resisting structure comprises:
a plurality of zones of the rubber bush that are equally partitioned, the number of zones corresponding to the number of the lead wires, each zone of the rubber bush having a center position through which the corresponding lead wire passes, and
wherein the heat resisting structure is constructed to satisfy the following inequality:

$10\% \leq Al/Ar \leq 50\%$ wherein:
Al: The sectional area in total of the lead wires; and
Ar: The sectional area of the rubber bush.

9. An oxygen sensor as claimed in claim 8, in which the heat resisting structure is constructed to satisfy the following inequality:

$10\% \leq Al/Ar \leq 30\%$.

10. An oxygen sensor as claimed in claim 8, in which the heat resisting structure is constructed to satisfy the following inequality;

$$Ac/Al \geq 40\%$$

wherein:
Ac: The sectional area in total of the core wires of the lead wires; and
Al: The sectional area in total of the lead wires.

11. An oxygen sensor as claimed in claim 10, in which over 50% in weight of the material of the core wires is constructed of a metal of which heat conductivity is higher than 300 W/m·K.

12. An oxygen sensor as claimed in claim 1, in which the rubber bush is made of a fluoro rubber.

* * * * *